United States Patent
Nelson et al.

(10) Patent No.: US 9,546,381 B2
(45) Date of Patent: Jan. 17, 2017

(54) USE OF ANTICOAGULANTS IN THE PRODUCTION OF RECOMBINANT PROTEINS IN THE MILK OF TRANSGENIC ANIMALS

(75) Inventors: Kathryn Margaret Nelson, DeForest, WI (US); Michael William Mosesson, Milwaukee, WI (US); Anthony Pusateri, Hillsborough, NJ (US); Erik Jordahl Forsberg, Fitchburg, WI (US)

(73) Assignee: PHARMING INTELLECTUAL PROPERTY BV (NL)

( * ) Notice: Subject to any disclaimer, the term of this patent is extended or adjusted under 35 U.S.C. 154(b) by 501 days.

(21) Appl. No.: 13/582,044

(22) PCT Filed: Mar. 11, 2011

(86) PCT No.: PCT/NL2011/050166
§ 371 (c)(1),
(2), (4) Date: Nov. 6, 2012

(87) PCT Pub. No.: WO2011/115479
PCT Pub. Date: Sep. 22, 2011

(65) Prior Publication Data
US 2013/0053546 A1    Feb. 28, 2013

Related U.S. Application Data

(60) Provisional application No. 61/314,673, filed on Mar. 17, 2010, provisional application No. 61/387,665, filed on Sep. 29, 2010.

(30) Foreign Application Priority Data

Mar. 17, 2010   (EP) ..................................... 10156751

(51) Int. Cl.
*C12N 15/85*  (2006.01)
*A61K 31/37*  (2006.01)
*C07K 14/75*  (2006.01)

(52) U.S. Cl.
CPC ........... *C12N 15/8509* (2013.01); *A61K 31/37* (2013.01); *C07K 14/75* (2013.01); *A01K 2267/01* (2013.01)

(58) Field of Classification Search
CPC ............... C12N 2015/8518; C12N 2015/8509; A61K 31/37; C07K 14/75
See application file for complete search history.

(56) References Cited

FOREIGN PATENT DOCUMENTS

| WO | WO 95/22249 A1 | 8/1995 |
| WO | WO 95/23868 A1 | 9/1995 |
| WO | WO 00/30436 A1 | 6/2000 |

OTHER PUBLICATIONS

Clark et al., "Coumarin derivatives and breast-feeding," Obstetrics & Gynecology, 95(6, Part 1):938-940, (2000).
Clark et al., "Pharmaceuticals from transgenic livestock," TIBTECH, 5:20-24, (1987).
Domján et al., "Anticoagulation in obstetrics," LAM, 16(5):419-426, (2006).
EP Extendeded European Search Report for application EP10156751.9 mailed Jul. 27, 2010.
Niemann et al., "Transgenic farm animals: an update," Reproduction Fertility and Development, 19(6):762-770, (2007).
PCT International Search Report for application PCT/NL2011/050166 mailed Jul. 6, 2011.
PCT International Preliminary Report on Patentability for application PCT/NL2011/050166 issued Sep. 18, 2012.

*Primary Examiner* — Marsha Tsay
(74) *Attorney, Agent, or Firm* — Alston & Bird LLP

(57) ABSTRACT

The invention relates to the production of recombinant human fibrinogen (rhFib) in the milk of transgenic mammalian animals. This production and subsequent purification process is generally hampered by the occurrence of so-called 'clots' and 'flakes' in the milk which, in severe cases, may prevent the cow from being milked at all, resulting in a halt of lactation. These clots and flakes occur because of the expression of the fibrinogen protein, which is a factor that is normally involved in blood clotting. The invention relates to solving this milk clotting problem by treating the (lactating) animals with anticoagulants such as coumarins. A preferred anticoagulant that is used in the methods of the present invention is warfarin.

15 Claims, No Drawings

USE OF ANTICOAGULANTS IN THE PRODUCTION OF RECOMBINANT PROTEINS IN THE MILK OF TRANSGENIC ANIMALS

CROSS REFERENCE OF RELATED APPLICATION

This application is a U.S. National Phase application filed under 35 U.S.C 371 of International Application No. PCT/NL2011/050166; filed Mar. 11, 2011, which claims the benefit of U.S. Provisional Application No. 61/314,673; filed Mar. 17, 2010; European Application No. 10156751.9; filed Mar. 17, 2010; and U.S. Provisional Application No. 61/387,665; filed Sep. 29, 2010.

FIELD OF THE INVENTION

The invention relates to the field of medicine. In particular it relates to the use of transgenic mammalian animals to produce medicinal products. More in particular it relates to the use of certain compounds such as anticoagulants in improving the production of recombinant proteins, preferably proteins involved in blood clotting such as fibrinogen, in the milk of transgenic animals.

BACKGROUND OF THE INVENTION

Fibrinogen, the main structural protein in the blood responsible for the formation of blood clots, exists as a dimer of three polypeptide chains; the A$\alpha$ (66.5 kD), B$\beta$ (52 kD) and $\gamma$ (46.5 kD) chains are linked through 29 disulphide bonds. The addition of asparagine-linked carbohydrates to the B$\beta$ and $\gamma$ chains results in a molecule with a molecular weight of 340 kD. Fibrinogen has a trinodal structure. A central nodule, termed the E domain, contains the amino-termini of all 6 chains including the fibrinopeptides (Fp) whereas the two distal nodules termed D domains contain the carboxy-termini of the A$\alpha$, B$\beta$ and $\gamma$ chains. Fibrinogen is proteolytically cleaved at the amino terminus of the A$\alpha$ and B$\beta$ chains releasing fibrinopeptides A and B (FpA & FpB) and converted into a fibrin monomer by thrombin, which is a serine protease that is converted from its inactive form by Factor Xa. The resultant fibrin monomers non-covalently assemble into protofibrils by DE contacts on neighboring fibrin molecules, and as a result clots are formed. Patients with a fibrinogen deficiency (either hereditary or acquired) suffer from increased levels of bleeding resembling phenotypes seen in moderate or mild hemophilia.

There has been a need for medicinal fibrinogen to treat increased bleeding or bleeding caused by fibrinogen deficiency. Several sources have been studied and used to produce the molecule, such as purification from human plasma (from donor blood) or through the production of recombinant fibrinogen in prokaryotic cells, eukaryotic cell systems and in the milk of transgenic animals. Although purification of fibrinogen directly from human plasma appeared to be useful, it is accompanied by several potentially severe problems due to the possible presence of human blood-related pathogens such as HIV and others. In addition plasma derived fibrinogen is not consistent in its clotting and cohesion kinetics. The production of recombinant fibrinogen is also hampered by the fact that the protein structure is rather complex as outlined above. The molecule is heavily glycosylated, and it appeared that this glycosylation is of key importance in the functionality of the protein, which makes production on prokaryotes ineffective. The production of fibrinogen in a culture of eukaryotic cells generally resulted in very low yields, which was an indication that such systems could also not provide enough protein for therapeutic use. The solution to these production problems was found in the use of transgenic animals (such as lactating cows) that appeared to be able to produce high concentrations of functional fibrinogen in their milk (WO 95/23868; WO 95/22249).

Although production levels in transgenic mammalian animals are generally high, these animals often experience precipitation of the fibrinogen in the milk (reported as 'flakes' and 'clots'), most likely due to activation of the protein within the mammary gland. This hampers lactation as well as purification of the active molecule. Historically it has been documented that cattle, mice and sheep transgenic for recombinant human fibrinogen (also herein referred to as rhFIb) and expressing it in their milk, often had clots and flakes in their milk. The degree of flakes and clots appears to vary per animal, by expression level, by quarter, and by stage of lactation. Moreover, the degree of aggregation (clotting) can vary on a daily basis and is problematic to control. As far as the inventors are aware, clotting of the milk in animals only occurs upon mastitis, an inflammation of the quarters in the udder.

Clearly, as indicated, such clots trouble the release of milk from the transgenic female animal itself. Moreover, because such aggregation of the transgenically produced fibrinogen hampers the downstream purification process and—through this—lowers the final production level, there is a strong need for compounds and methods and that could prevent this appearance of fibrinogen aggregation and the occurrence of fibrinogen flakes and clots in the milk of animals that are transgenic for rhFib.

SUMMARY OF THE INVENTION

The present invention relates to methods for the production of a recombinant blood clotting factor (preferably recombinant human fibrinogen) in the milk of a transgenic mammalian animal, wherein said animal is transgenic for said recombinant blood clotting factor and wherein said recombinant blood clotting factor is expressed in the milk of said transgenic animal, comprising the steps of starting lactation in said animal, administering an anticoagulant to said animal, and harvesting from said animal the milk containing said recombinant blood clotting factor. The preferred animal according to the present invention is a cow and the preferred anticoagulant used in the methods and uses of the present invention is a coumarin-derived anticoagulant, more preferably warfarin. The methods of the present invention may further optionally comprise the steps of purifying said recombinant blood clotting factor from said milk, and/or determining the degree of clots and flakes in the milk of said animal.

The invention also relates to methods for the treatment of an animal that is transgenic for a recombinant blood clotting factor, wherein said recombinant blood clotting factor is produced in the milk of said animal, comprising the steps of starting lactation in said animal, and administering an anticoagulant to said animal. Furthermore the invention relates to methods for the prevention of the occurrence of clots and flakes in the milk of an animal that is transgenic for a recombinant blood clotting factor being produced in said milk, comprising the steps of starting lactation in said animal, and administering an anticoagulant to said animal.

The invention also relates to warfarin for use in the treatment of preventing or inhibiting the occurrence of clots and/or flakes in the milk of a transgenic animal, preferably a cow, wherein said animal is transgenic for a recombinant blood clotting factor, preferably rhFib, that is produced in said milk.

In another embodiment, the present invention relates to a use of an anticoagulant, preferably warfarin, in the preparation of a medicament for the treatment of an animal, preferably a cow, that is transgenic for a recombinant blood clotting factor, that is preferably rhFib. In yet another embodiment, the present invention relates to the use of an anticoagulant according to the embodiments of the present invention in the preparation of a medicament for the inhibition of flake- and/or clot formation in the milk of a female transgenic animal, preferably a cow, wherein said transgenic animal produces a recombinant blood clotting factor in her milk.

DETAILED DESCRIPTION

The inventors of the present invention have found, and now disclose for the first time herein, that when providing an anticoagulant to transgenic animals that produce recombinant human fibrinogen in their milk, the appearance of the flakes and clots of aggregated and/or activated fibrinogen in the milk can be significantly reduced, and even be brought back to undetectable levels. This treatment resulted in an improved lactation for the animals, and in an improved purification process (because the milk did not plug the purification filters any earlier than normal milk from non-transgenic animals). Importantly, this treatment resulted in a higher yield of fibrinogen after purification.

Recombinant human fibrinogen has been produced in the milk of transgenic cows for some years now. It was found that this blood clotting factor in numerous cases caused a degree of clotting in the milk. Moreover, similar clotting events were seen in transgenic mice and sheep (non-published internal results). To score the level of clotting and to measure any effects, standards were set to determine whether treatment of the cows to reduce clotting was indeed effective. The standards are provided in Table I. Score level 0 is equal to normal milk from non-transgenic cows, whereas score level 4 equals a dramatic level of clotting and the milking machine is unable to extract the milk from the teat. CMT stands for 'California Mastitis Test' and is a standard cow side test that screens for the presence of mastitis, a known cause of milk clotting. When a cow is milked, the milk is collected in a so-called CMT paddle, which has four cups corresponding to the four quarters of the udder. To these cups, equal amounts of CMT solution (made up of a detergent to break down cell walls, a compound that reacts with the cellular DNA and a pH indicator; California Mastitis Test kit, TechniVet, Brunswick, Me.) is added after which the solution is swirled. The CMT solution provides an estimate of the number of cells in the milk (inflammatory cells due to infection by mastitis). As the cell content increases the mixture becomes thick and gel-like and the results are based on the appearance of the solutions. 'Negative' in the mastitis test means that the mixture remains fluid; 'suspicious' means that the mixture becomes slimy or gel like, and 'positive' means that the mixture distinctly forms a gel or jelly. When clotting was seen in the milk of the transgenic rhFib cattle the CMT test always turned out negative, indicating that the clotting was not caused by mastitis. The lack of mastitis was also confirmed by the fact that in laboratory tests no inflammatory-inducing bacteria were grown from the rhFib transgenic cow milk. Finally the clinical signs of the cows confirmed that infectious mastitis was not the etiology of the clotting. These cows did not have fevers, decreased appetites and nor did they have painful, inflamed mammary glands which are typically seen in cases of mastitis. The (blue) staining by the CMT solution provided a useful tool to visualize the clots and helped to distinguish between some of the low scores of rate 1 and 2.

A cow's udder has four quarters, each with their own teat. A cow may loose a quarter due to mastitis but still give milk through the remaining quarters. It has been found that in certain cows not all four quarters gave milk that contained clots and flakes, but that for instance two out of four gave milk with clotting. Therefore at each milking period, each quarter was given a clot score and recorded on her milk sheet form. The highest score on the paddle for each day was considered the cow's score for that day when complying the clotting data.

Notably, when a cow scores 4 on this clot scoring standard list, the problems are quite severe: the milk can no longer be removed with the milking machine and the milk needs to be stripped by hand. Even then, it is not always possible to get the milk out, resulting in a discomfort for the animal. Moreover, if the milk cannot be removed from the udder, due to such high clot scores, lactation ceases and may eventually stop. Stripping by hand may also lead to injuries of the teat sphincter, which would interfere with milk removal at subsequent lactations regardless of the clot score. Hence, there is a great need to prevent the occurrence of clots and flakes in the milk of these transgenic cows to ensure comfort to the cows and a proper production of milk, and rhFib contained therein.

TABLE I

Clot scoring standards

0. Normal milk
    No clots or flakes are seen either with or
    without the CMT solution added
1. Flakes
    Flakes are not seen until CMT solution is added
    Milk can be removed from the mammary
    gland with the milk machine
2. Less than 10 clots from the quarter on the CMT paddle
    Clots are visible before the CMT solution is added
    Milk can be removed from the mammary
    gland with the milk machine
3. Greater than 10 clots from the quarter on the CMT paddle
    Clots are visible before the CMT solution is added
    Milk can be removed from the mammary
    gland with the milk machine
4. Severe visible clots
    Need to hand strip
    Milk cannot be removed from the mammary
    gland with the milk machine An anticoagulant is a substance that prevents coagulation: that is, it stops blood from clotting. Anticoagulants can be used in vivo as a medication for thrombotic disorders and are generally given to people to stop thrombosis (blood clotting in the blood vessels). Many anticoagulants that are known in the art are coumarin-derived. Coumarin is a chemical found naturally in many plants, notably woodruff and at lower levels in licorice, lavender, and various other species. Examples of coumarin-derived anticoagulants (also referred to as coumarines) include, but are not limited to warfarin, phenindione, acenocoumarol, and phenprocoumon. A preferred coumarin-derived anticoagulant that is used in the methods of the present invention is warfarin. Other anticoagulants that may be used in the methods according to the present invention are heparin, rivaroxaban, fondaparinux, apixaban, betrixaban, and direct thrombin inhibitors such as argatroban, lepirudin, bivalirudin, and dabigatran.

Coumarines decrease blood coagulation by inhibiting vitamin K epoxide reductase, an enzyme that recycles oxidized vitamin K to its reduced form after it has participated in the carboxylation of several blood coagulation proteins, mainly prothrombin and Factor VII. For this reason, drugs in this class are also referred to as 'vitamin K antagonists'. As a consequence, all methods and uses of the present invention also relate to the application of vitamin K antagonists.

The preferred coumarin-derived anticoagulant according to the present invention, warfarin, was initially marketed as a pesticide against rats and mice. Later, it was found to be effective and relatively safe for preventing thrombosis and embolism in many disorders. It is a compound known since 1948 and was approved for use as a medication for humans in 1954. It is still the most widely prescribed anticoagulant drug in North America. In 1978 its mode of action was revealed when it was found that warfarin interfered with vitamin K metabolism. Warfarin is prescribed to people with an increased tendency for thrombosis or as a secondary prophylaxis (prevention of further episodes) in those individuals that have already formed a blood clot (thrombus). Warfarin treatment can help prevent formation of future blood clots and help reduce the risk of embolism (migration of a thrombus to a spot where it blocks blood supply to a vital organ). Common clinical indications for warfarin use are atrial fibrillation, the presence of artificial heart valves, deep venous thrombosis, pulmonary embolism, antiphospholipid syndrome and, occasionally, after heart attacks (myocardial infarction).

It is notable that warfarin medication tends to narrow therapeutic range. Dosing of warfarin is complicated by the fact that it is known to interact with many commonly-used medications and even with chemicals that may be present in certain foods. These interactions may enhance or reduce warfarin's anticoagulant effect. In order to optimize the therapeutic effect without risking dangerous side effects such as bleeding, close monitoring of the degree of anticoagulation is required by blood testing. During the initial stage of treatment, checking may be required daily; intervals between tests can be lengthened if the treated subject manages stable therapeutic International Normalized Ratio (INR) levels on an unchanged warfarin dose. Intra, Prothrombin Times (PT) have been used. Persons skilled in the art have been using this standardization method for many years. The INR was developed at the Karolinska Institute (Sweden) to reduce variability in PT results that was observed when measured by different laboratories. For example, the measured PT might be 18 seconds at one institution, 20 seconds at another and 16 seconds at a third institution. The INR standardizes the methods for comparison amongst those different sites. By running the patients blood test against a known standard, a value can be calculated which is more consistent from place-to-place than the traditional PT values were. Generally however, using PT is the most popular method of monitoring therapy and can be used when determined at a single site.

Coumarines, such as warfarin, are teratogens: they cause birth defects. Warfarin is therefore contraindicated in pregnancy, as it passes through the placental barrier. It may cause bleeding in the fetus. Warfarin use during pregnancy is commonly associated with spontaneous abortion, stillbirth, neonatal death, and preterm birth.

The only common side effect of warfarin is hemorrhage (bleeding). The risk of severe bleeding is however small. Risk of bleeding is augmented if the INR is out of range (due to accidental or deliberate overdose or due to interactions), and may cause hemoptysis, excessive bruising, bleeding from nose or gums, or blood in urine or feces. Other severe side effects that are rare but have been reported in both humans and animals are: anemia, thrombocytopenia, weakness, hematomas, ecchymosis, epistaxis, hematemesis, hematuria, melena, hematochezia, hemathrois, intracranial and/or pericardial hemorrhage and death. The risk of bleeding is increased when warfarin is combined with antiplatelet drugs such as clopidogrel, aspirin, or other nonsteroidal anti-inflammatory drugs.

It is known in the art that warfarin inhibits the vitamin K-dependent synthesis of biologically active forms of the calcium-dependent clotting Factors II, -VII, -IX and -X, as well as the regulatory factors protein C, protein S, and protein Z. The precursors of these factors require carboxylation of their glutamic acid residues to allow the coagulation factors to bind to phospho lipid surfaces inside blood vessels on the vascular endothelium. The enzyme that carries out the carboxylation of glutamic acid is gamma-glutamyl carboxylase. The carboxylation reaction will proceed only if the carboxylase enzyme is able to convert a reduced form of vitamin K (vitamin K hydroquinone) to vitamin K epoxide at the same time. The vitamin K epoxide is in turn recycled back to vitamin K and vitamin K hydroquinone by another enzyme, the vitamin K epoxide reductase (VKOR). Warfarin inhibits epoxide reductase, thereby diminishing available vitamin K and vitamin K hydroquinone, which inhibits the carboxylation activity of the glutamyl carboxylase. When this occurs, the coagulation factors are no longer carboxylated at certain glutamic acid residues, and are incapable of binding to the endothelial surface of blood vessels, and are thus biologically inactive. As the body's stores of previously-produced active factors degrade (over several days) and are replaced by inactive factors, the anticoagulant effect becomes apparent. The coagulation factors are produced, but have decreased functionality due to undercarboxylation; they are collectively referred to as PIVKA's: proteins induced by vitamin K absence/antagonism. The end result of warfarin use, therefore, is to diminish blood clotting in the patient.

The inventors of the present invention asked themselves whether the problem of the appearance of fibrinogen-induced flakes and clots in the milk of rhFib transgenic animals could be prevented by the use of compounds that are commonly and solely used in medicaments to decrease the clotting of blood in blood vessels, in other words: would the anticoagulants as discussed in detail above, also be active in the udder. Surprisingly, as outlined in the examples herein, it appeared that the administration of the coumarine warfarin, which is one of the anti-coagulants that have been used for several centuries against blood clotting indeed did lower the occurrence of flakes and clots in the milk of the transgenic cows to very low and even undetectable levels. This use of the anticoagulant resulted in complete milk removal (without the animal discomfort of removing clotted milk from the mammary glands), an improved total milk production level, and an increase in fibrinogen yield since the rhFib was not being activated to fibrin and fibrin degradation products. Due to a reduction in plugging of the purification filters, the methods of the present invention therefore also provide an overall improved fibrinogen production process.

The inventors also used heparin therapy in one transgenic cow to evaluate if it would prevent clot formation at a dose of 150 IU/kg SQ twice a day, for 5 days. While when the heparin was administered to this cow, the clot scores decreased. When the heparin therapy was discontinued, the clot scores remained low and decreased further with time, indicating another lack time and possibly another mode of action by this anticoagulant but also clearly showing that different anticoagulants are useful in the methods and uses of the present invention. However, due to the high costs of using heparin, that treatment was not further investigated. Other anticoagulants can be used but many have the disadvantage that they need to be injected intravenously or subcutaneously rather than be or administered orally. The preferred anticoagulant that is used in the methods of the invention is administered orally, not very often (for instance only once a day), have a low cost, is allowed for use in humans, and/or does not result in many or severe side-effects.

The present invention relates to a method for the production of a recombinant blood clotting factor in the milk of a transgenic (mammalian) animal, wherein said animal is transgenic for said recombinant blood clotting factor and wherein said recombinant blood clotting factor is expressed in the milk of said transgenic animal, comprising the steps of: starting lactation in said animal; administering an anticoagulant to said animal; and harvesting from said animal the milk containing said recombinant blood clotting factor. Generally, transgenic animals are used in the art to produce proteins in their milk for the application in humans to treat protein deficiencies. Therefore, in a preferred embodiment, said blood clotting factor is a human blood clotting factor. More preferably, said blood clotting factor is recombinant human Fibrinogen (herein also referred to as rhFib). Harvesting said milk from said transgenic animals is generally performed according to methods known in the art, often, when milking of cows, goats or other large animals are concerned by the using milking machines that collect the milk directly from the udder. May different kinds of transgenic animals have been produced in the art. Depending on the need of the final product and/or the potential commercial market for the medicament that could be targeted with such product, or the amount of product needed for research purposes, animals are chosen that would provide sufficient amounts of milk and recombinant protein contained therein. In a preferred embodiment of the methods and uses of the present invention, said transgenic animal is a bovine (preferably cattle), a sheep, a goat, a rabbit, a pig or a murine (preferably mice) animal. The most preferred animal that is used in the methods of the present invention is a transgenic cow, or transgenic heifer.

It is clear that not all animals lactate, but that only mammals that produce milk to naturally feed their offspring are regarded as 'lactating animals' comprised within the scope of protection conferred by the methods, uses and compounds of the present invention. For this, 'animals' as used herein are limited to animals that are able to produce milk: hence, where the word 'animal' or 'animals' is used herein related to the present invention, this relates to a 'mammalian animal' or 'mammals', not including humans.

Female mammalian animals do not always lactate. The start of lactation may come naturally, upon pregnancy and after giving birth (calving in the case of cows), but may also be induced by administration of hormones. It is important to note that as used herein, 'starting of lactation' does not refer solely to a chemical or hormonal induction. Lactation may also be started through natural ways, upon giving birth after a normal pregnancy without chemical interference or stimulation. Methods for lactation induction by chemical, or (synthetic or recombinant) hormones are known in the art. Depending on the need for offspring or on the need of milk containing the recombinant protein, one can decide to either wait for lactation to occur after a natural pregnancy or induce lactation synthetically. When milk (generally for research purposes only) is needed rather than new animals, lactation induction by chemical means (administration of hormones) is preferred in the methods and uses according to the present invention. Herein, when lactation is referred to as 'natural' this means that the animal was pregnant and started lactation upon giving birth, which may also be the preferred way to initiate lactation in the event that it is needed that the animal gets offspring to generate new transgenic animals. In general, because often milk consumption after chemical induction is not allowed in many countries, the preferred method for producing rhFib for the production of medicaments and/or human intake, is by a natural start of lactation through normal pregnancy, and upon calving in the case of cows.

Many different anticoagulants are known in the art. Any of the known anticoagulants of the art can be applied in the methods of the present invention. Preferred anticoagulants are coumarin-derived anticoagulants, such as warfarin, phenindione, acenocoumarol and phenprocoumon. A particularly preferred anticoagulant that is being used in the methods and uses according to the present invention is warfarin as this anticoagulant is administered orally, it is not very expensive, known for many years and allowed for use in humans, which also makes it a relatively safe compound. In a particular embodiment, the invention relates to methods and uses according to the invention wherein warfarin is administered in a dose that prevents the appearance of clots and flakes in the milk, and preferably at a dose between about 0.010 mg/kg/day and about 0.18 mg/kg/day, more preferably in a dose between about 0.10 mg/kg/day and about 0.14 mg/kg/day, and even more preferably in a dose between about 0.10 mg/kg/day and about 0.13 mg/kg/day. These dosages are preferably used when the transgenic animal is cattle, preferably a cow.

Other anticoagulants that may be used in the methods and uses of the present invention are heparin, rivaroxaban, fondaparinux, apixaban, or betrixaban, or compounds also referred to as direct thrombin inhibitors such as argatroban, lepirudin, bivalirudin, and dabigatran. The list of anticoagulants as provided here is not limiting, as any anticoagulant may be applied in the methods and uses of the present invention. Depending on the transgenic animal, one can select a preferred anticoagulant with respect to administration, however, in a preferred embodiment, said anticoagulant is administered orally to said animal. In another embodiment of the present invention a mixture of (any of the above) anticoagulants is administered to said animal.

The invention also relates to method for the production of a recombinant blood clotting factor in the milk of a transgenic animal, wherein said method further comprises the optional step of purifying said recombinant blood clotting factor from said milk. Such purification is performed according to methods known to the person skilled in the art. The exact purification scheme and steps of blood clotting factors, such as the preferred protein rhFib, is outside the scope of the present invention but is generally according to methods known in the art. In another embodiment of the present invention, said methods comprise the further step of determining the degree of clots and flakes in the milk of said animal. According to Table I as provided intra, a person skilled in the art can determine the degree of clots and flakes that appear in the milk, which may subsequently hamper the lactation itself, the harvesting of milk and/or obtaining the recombinant blood clotting factor from the milk. Therefore, in another embodiment of the present invention, the amount of anticoagulant that is administered is related to the degree of clots and/or flakes in the milk of the transgenic animal.

The invention also relates to a method for the treatment of an animal that is transgenic for a recombinant blood clotting factor, wherein said recombinant blood clotting factor is produced in the milk of said animal, comprising the steps of starting lactation in said animal and administering an anticoagulant to said animal. In yet another embodiment, the invention relates to a method for the prevention of the occurrence of clots and flakes in the milk of an animal that is transgenic for a recombinant blood clotting factor being produced in said milk, comprising the steps of starting lactation in said animal and administering an anticoagulant to said animal.

The invention relates to an anticoagulant for use in the treatment of preventing or inhibiting the occurrence and/or formation of clots and/or flakes in the milk of a transgenic animal, wherein said animal is transgenic for a recombinant blood clotting factor that is produced in said milk. Preferably, said anticoagulant is warfarin. Also preferred is an anticoagulant for such use, wherein said blood clotting factor is recombinant human Fibrinogen (rhFib). Furthermore, preferably said animal is a cow, a sheep, a goat, a rabbit, a pig or a mouse. Even more preferably, said animal is a female cow. In other words, the invention also relates to an anticoagulant for use in the treatment of a transgenic mammalian animal that is transgenic for a recombinant blood clotting factor being produced in the milk of said animal, to prevent or inhibit the occurrence or formation of clots and/or flakes in the milk of said animal, which is caused by the fact that the animal is transgenic to produce said recombinant blood clotting factor. The milk is preferably produced naturally upon calving, but may also be synthetically induced upon administering hormones.

In yet another preferred embodiment, the anticoagulant is heparin, rivaroxaban, fondaparinux, apixaban, or betrixaban, or a direct thrombin inhibitor such as argatroban, lepirudin, bivalirudin, and dabigatran. Preferably, the anticoagulant according to the invention is administered orally.

The invention also relates to the use of an anticoagulant in the preparation of a medicament for the treatment of an animal that is transgenic for a recombinant blood clotting factor. Preferably, said recombinant blood clotting factor is a human blood clotting factor, and even more preferably, said blood clotting factor is recombinant human Fibrinogen (rhFib). In a preferred embodiment of the use according to the present invention said animal is a bovine (preferably cattle, and even more preferably, a cow), a sheep, a goat, a rabbit, a pig or a murine (preferably mice) animal. In another preferred embodiment, the invention relates to a use according to the invention wherein said anticoagulant is a coumarin-derived anticoagulant, such as warfarin, phenindione, acenocoumarol and phenprocoumon. A preferred coumarin-derived anticoagulant is warfarin. In yet another embodiment, said anticoagulant is heparin, rivaroxaban, fondaparinux, apixaban, or betrixaban, or a direct thrombin inhibitor such as argatroban, lepirudin, bivalirudin, and dabigatran.

Furthermore, the invention relates to the use of an anticoagulant according to the present invention in the preparation of a medicament for the inhibition of flake- and/or clot formation in the milk of a female transgenic animal, wherein said transgenic animal produces a recombinant blood clotting factor, preferably a human blood clotting factor, and even more preferably rhFib, in her milk.

The invention also relates to the milk obtained by a method according to any one of the methods or uses according to the invention, as it is preferred to obtain milk that does not contain flakes and clots, which ensures an easier handling of the milk and purification of the final product. Although the clots- and flake scoring method described herein is a useful tool to measure and determine a degree of milk clotting, it is up to the scoring person to set that degree. Clearly, more clot- and flake-free milk is obtained by the methods and uses according to the present invention. The present invention now enables one to obtain such clot- and flake-free milk from the transgenic animals and provides new methods and uses to finally obtain purified recombinant blood clotting factors from such animals in a more convenient manner.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that an anticoagulant or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (about 10) preferably means that the value may be the given value of 10 more or less 0.1% of the value.

All patent and literature references cited in the present specification are hereby incorporated by reference in their entirety.

The following examples are offered for illustrative purposes only, and are not intended to limit the scope of the present invention in any way.

EXAMPLES

Example 1

Determination of Warfarin Dosing

An initial experiment was performed to determine a dose range of warfarin in cattle. Current doses for warfarin are listed in the Veterinary drug handbook (Plumb 1999) for cats, dogs and horses. The doses therein range from 0.012 to 0.57 mg/kg. The $LD_{50}$ for cattle is 200 mg/kg/day for 5 days. Prowse et al. (1976) disclosed a dosing of 100 mg/cow for over 90 days with no description of adverse affects.

Two non-transgenic non-lactating cows (referred to as #4289 and #6685) were used to determine a proper warfarin dose for cattle, and thus to determine the subsequent correct and safe dose for treatment of transgenic cows producing recombinant human fibrinogen (rhFib). An initial baseline Prothombin time (PT time) and Hematocrit (Hct) were determined. For cow #4289 Hct was 38 and PT was 25.9 seconds. For cow #6685 Hct was 27 and PT time was 26.7 seconds. PT time is a laboratory assay that reflects the depression of vitamin K dependent Factors II, -VII and -X. The PT times were used to determine the final dosing. The PT time test that is generally used in the art, looks at coagulation factors Factor I (fibrinogen), Factor II (prothrombin), Factor V, Factor VII and Factor X, that are all involved in clotting. The test measures the time it takes for a patient's blood to clot. Warfarin, via its Vitamin K routed effects will decrease Factors II, VII, and X levels and therefore will cause the PT times to be prolonged. The Hct value is helpful to determine if the animal is becoming anemic (i.e. blood loss that would not be grossly evident). In general, Hct is not checked unless one is concerned that blood loss is occurring.

Initially a dose necessary to double the baseline PT times was to be determined and then the dose was to be increased to monitor for adverse affects. It was decided that if the PT levels began to be prolonged over 2.5 times baseline, or Hct fell below 15% the dose would be decreased. Likewise, it was held that the dose would be decreased or discontinued if any of the following disorders would appear: hematomas, anemia, epistaxis, hematemesis, hematuria, melena, hemathrosis, hemothrax, weakness or hematochezia, or bleeding within the udder. Therapy with vitamin K1 and whole blood would be initiated if there was evidence of non-life threatening bleeding. In the event that the cattle exhibited life-threatening hemorrhage they would immediately be humanely euthanized.

Warfarin (anticoagulant tablets containing 10 mg of warfarin sodium; Taro, Hawthorne, N.Y., USA) was given orally once a day in the mornings by putting the required dose into a gel capsule and using a rubber ended balling gun. Because of teratogenic effects discussed intra, pregnant women were not allowed to administer warfarin to the animals. Moreover, and for the same reason, pregnant animals were also not treated with warfarin.

The first cow (referred to as #4289) was given warfarin at 10 mg/day (~0.014 mg/kg) orally once a day during the morning feedings. The dose was increased by 10 mg/day until a dose of 100 mg/day was given (~0.14 mg/kg). Then, this dose was maintained for 12 days. Unfortunately, this experiment showed that PT times varied too widely to make dose adjustments. It also appeared that the tail vein was a poor vein to sample PT as it resulted in inconsistent values. Therefore the following adjustments were made: First, the animal was sedated with xylazine, and second, blood was only collected from the jugular vein while the animal's head was tightly restrained. The dose was increased to 120 mg/day (~0.17 mg/kg) for 17 days. During this treatment, no adverse effects were observed. Then, the dose was increased to 130 mg/day (~0.18 mg/kg) for 6 days and the animal developed a bleeding hematoma over the shoulder/thorax and was subsequently euthanized.

The second cow (referred to as #6685) began warfarin therapy at 100 mg/day (~0.18 mg/kg) which continued for 14 days. No adverse affects were found. It took 6 days of therapy for the PT times to double. This therapy was discontinued at the time cow #4289 exhibited the bleeding complications (which was at day 14). For this reason, this dose of approximately 0.18 mg/kg was then considered unsafe for use in the transgenic rhFib cows.

Over time and before treatment with warfarin was even contemplated by the inventors, it was observed that transgenic rhFib cow #13 (also referred to with the name 'Fantasy') developed clots during her first and second natural lactation. For clot standards see Table I above, which was used to score clotting in the rhFib milk. This cow, during her first natural lactation, was milked for 180 days, and gave an average of 20 liters/day, and had clot scores of 3 during the first week of lactation which resolved over the extended milking period. However, after calving for the second time, cow #13 developed clot scores of 4 in all 4 quarters on day 8 of lactation and because the milk could not be stripped out of the udder, lactation was abandoned.

With natural lactation, it is common for cattle to develop swelling and edema in their udders around the time of calving and as they "come into milk" during the first few weeks of lactation. This inflammation of the mammary tissue may activate the rhFib and lead to precipitation within the mammary tissue. This then may lead to a decrease in the milk production and difficulty in removing the milk from the gland. It was hypothesized by the inventors that by a non-natural lactation (that is: by a chemical/hormonal lactation induction), this udder swelling and edema would be avoided and the rhFib would not be activated. This would facilitate an easier lactation with minimal precipitation. For this reason, lactation induction was chosen to produce rhFib in cow #13. Hence, this cow was induced to lactate using a progesterone/estradiol and dexamethasone solution known in the art (Smith and Schanbacher, 1973) given over a 16 day period before initiating milking.

Unexpectedly, within 16 days of milking her clot scores rose instantly from 0 to 1 in the rear quarters to clot scores of 3 and 4, and two days later the lactation was abandoned due to inability to remove the milk from the mammary glands. It was for this reason that this specific cow #13 was first selected and induced to lactate again 7 months later in order to investigate the effect of warfarin and to see whether the clot score could be reduced using warfarin treatment.

Immediately following injections for the lactation induction cow #13 was given warfarin orally, once a day, at a dose of 0.13 mg/kg on the day that milking began (Time 0). After this, all clot scores remained between 0-1. Due to variations in the PT times, it was decided to lower the warfarin dose to 0.12 mg/kg at day 16. This dose was maintained during day 17 to day 31 and all clot scores still remained between 0-1. Warfarin was then discontinued for 19 days and clot scores increased to 2 (at day 30 of the milking period). Therefore warfarin therapy was re-initiated and 7 days later clot scores stabilized at level 1 and then over the next 11 days dropped to 0. Warfarin was again discontinued and 18 days later clot scores rose and maintained at level 2 until she was dried off. It was concluded from these observations that treatment with warfarin could lower clot scores to level between 0 and 1 within a week. It was also clear that when warfarin was no longer provided, clot scores increased again, which indicated that warfarin treatment needed to be continued to maintain low clot scores. No adverse effects were observed in cow #13 during the period she was treated with warfarin in the concentrations of 0.12 or 0.13 mg/kg per day. It was decided that a conservative, but safe and preferred dosage for future use in lactating rhFib transgenic cows would be about 0.10 to about 0.13 mg warfarin per kg per day.

Example 2

Treatment of rhFib Transgenic Cows and Heifers with Warfarin

Seven transgenic rhFib cattle were induced to lactate using an estradiol-progesterone alcohol solution and dexamethasone injections as outlined above. From these seven animals, after an initial 34 days of milking, five transgenic cattle were selected to complete an ongoing 16 week lactation period (146 days in total). During this 16 week period 5 liters of milk was saved per animal per week for future production purposes. If an animal was to develop consistent clotting within this production period then a treatment trial with warfarin would begin. Data was collected on these animals to see what level of clot scores they generally reached. One cow ('Foxy') produced low levels of milk and was only milking out 2 of her 4 quarters, probably because the other 2 quarters were damaged during natural lactation when she developed clot scores of 4. It was hypothesized that due to lack of edema and low milk production, she did not develop clots which she had in the past. This cow was not treated with warfarin.

Three heifers (referred to as #462: 'Fantasia', #463: 'Foxann' and #474 'Frey') all developed clot scores of 3 in their milk within 3 to 31 days upon induction of lactation and remained variable with sporadic clot scores of 3 in one or more quarters after that time period. Lactation should continue for a period of 16 weeks. Heifer #462 reached a clot score of 3 at day 3 and started warfarin intake at day 58; heifer #463 reached a clot score of 3 at day 7 and started warfarin intake at day 58; whereas heifer #474 reached a clot score of 3 at day 31 and started warfarin intake at day 66. Cow #60 (also referred to as 'Foxette') developed clot scores of 3 by day 16, however by day 30 these scores were consistently 2 or less, and dropped to 0 over a period of the following 50 days, and was never treated with warfarin.

Based on warfarin dosing data outlined in Example 1, an initial daily starting dose for the three rhFib-transgenic heifers was set at 0.10 mg/kg with monitoring of PT times weekly and for clinical signs of bleeding complications several times a day. If PT times were equal to or above twice the baseline value then the PT time would be evaluated the following day and if still high the warfarin discontinued for several days. This did not occur. If the clot scores would not decrease with this dose then an increase in the dosage could be given but the dosage would not go above 0.15 mg/kg daily. However, no increase in warfarin treatment appeared necessary.

TABLE II

Clot scores in the milk of three rhFib-transgenic heifers. Treatment with warfarin (0.10 mg/kg per day) started for #462 and #463 at day 58 of lactation, and for #474 at day 66 of lactation.

| Stage | #462 Fantasia Highest clot score | #463 Foxann Highest clot score | #474 Frey Highest clot score |
|---|---|---|---|
| Day 1-7 | 3 | 3 | 0 |
| Day 8-14 | 3 | 3 | 1 |
| Day 15-21 | 3 | 3 | 0 |
| Day 22-28 | 3 | 3 | 1 |
| Day 29-34 | 3 | 3 | 2 |
| Day 35-41 | 3 | 3 | 3 |
| Day 42-48 | 3 | 3 | 3 |
| Day 49-55 | 3 | 3 | 3 |
| Day 56-62 | 3 | 3 | 3 |
| Day 63-69 | 1 | 3 | 3 |
| Day 70-76 | 1 | 1 | 2 |
| Day 77-83 | 1 | 1 | 2 |
| Day 84-90 | 0 | 1 | 1 |
| Day 91-97 | 0 | 0 | 0 |
| Day 98-104 | 0 | 0 | 0 |
| Day 105-111 | 0 | 0 | 0 |
| Day 112-118 | 0 | 0 | 0 |
| Day 119-125 | 1 | 0 | 0 |
| Day 126-132 | 0 | 0 | 0 |
| Day 133-139 | 0 | 0 | 0 |
| Day 140-146 | 0 | 0 | 3* |
| Day 147-153 | 1 | 0 | 3 |
| Day 154-160 | 1 | 1 | Stopped milking |
| Day 161-167 | 3 | 3 | |

*indicates clot score in #474 after discontinuation of warfarin treatment on day 142 of lactation by which clot score increased to level 3 within 3 days after discontinuation.

Table II shows the results of clot scores before, during and after treatment with warfarin detected in the three transgenic heifers. During the initial 34 days, all milk was discarded due to the presence of the hormones that induced the lactation. Those hormones were no longer detectable after day 34. While #462 and #463 had a clot level of 3 within the first week of lactation induction, #474 reached score 3 later, around day 35. Warfarin treatment was started at day 58 of lactation in #462 and #463, while for #474, treatment was started at day 66 of lactation. As can be seen in the subsequent measurements, in all three cases, within a week after warfarin therapy was initiated the clot scores dropped to 1 and further down to 0. Within 23 to 28 days calculated from the start of warfarin treatment, all three heifers had clot scores of 0 for the remainder of the lactation, except for a single score of 1 in #462 at day 125. At day 142 of milking, warfarin treatment was stopped and clot scores in #474 increased to level 3 within 3 days (shown with an asterisk in Table II). Clot scores in #462 increased to level 1 at day 149 and her milk started to plug the filters during milk processing. At day 161 clot scores in #463 rose to 1 in a single quarter. During the dry off period that followed, the clot scores rose to level 3 in both #462 and #463.

From these experiments it was concluded that warfarin treatment of lactating cows that display flakes and clots due to the activation of blood clotting factors (in this case rhFib), can be decreased to undetectable levels, leading to easier lactations, and that purification of the protein of interest (in this case rhFib) from the milk is no longer hampered by any flakes and clots that plug filters, such that the final amount of purified protein may be increased.

Example 3

Levels of rhFib in the Milk of Warfarin-Treated Transgenic Heifers

The milk produced by the three warfarin-treated heifers of Example 2 was used to determine the amount of recombinant human fibrinogen contained therein. This determination was performed according to methods known to the person skilled in the art (such as disclosed in WO 00/17234) and more in particular according to the following general ELISA protocol:

(a) wells of a Maxisorp microtiter plate were coated with 100 µl coat solution containing 5 µg/ml goat anti-human fibrinogen IgG (Nordic Immunological Laboratories #GAHu/Fbg/7S) in PBS O/N at 4° C.;
(b) plates were washed 6× with PBS/0.02% Tween20;
(c) plates were blocked with 200 µl per well PCTE (PBS, 0.25% casein, 0.05% Tween20, 50 mM EDTA) for 1 h at RT, while shaking;
(d) plates were washed 6× with PBS/0.02% Tween20;
(e) wells were incubated with 100 µl calibration curve standard and two internal controls (already diluted 1:100) in PCTE that are further diluted as follows:
calibration curve (rhFib): 600-300-150-75-37.5-18.8-9.4-4.7 ng/ml
Internal Control 1: (Faye-milk) 15000-30000-60000× diluted
Internal Control 2: (Fancy-milk) 50000-100000-200000× diluted
Milk samples were diluted 1:10 by mixing 500 µl with 4500 µl PCTE and further diluted 1:10 in PCTE as required. Samples and controls were incubated for 1 h at RT while shaking;
(f) plates were washed 6× with PBS/0.02% Tween20;
(g) wells were then incubated with 100 µl conjugate solution containing peroxidise labelled goat anti-human fibrinogen IgG (Nordic Immunological Laboratories #GAHu/Fbg/PO), diluted 1:3000 in PCTE, for 1 h at RT while shaking;
(h) plates were washed 6× with PBS/0.02% Tween20;
(i) plates were incubated with 100 μl TMB/$H_2O_2$ substrate for 15 min at RT and then stopped with 2 M $H_2SO_4$;
(j) plates were measured at 450 nm with a PowerWaveX Select-I microtiterplate reader with KC-4 software The amount of milk that was produced did not significantly change over time, see Table III. The protein concentrations are in mg/ml raw milk. From Table III it becomes clear that over time and upon warfarin treatment, the concentration of rhFib seem to increase while clot score levels drop. This indicates that the reduction of flakes and clots by warfarin therapy leads to an increase in the amount of human blood clotting factor fibrinogen in the cow milk, i.e. more of the intact protein can be found in the milk, which is very beneficial for the entire process of producing this highly important medicinal protein from transgenic animals. As a consequence, higher yields of purified rhFib from the milk can be achieved.

TABLE III

Concentrations levels of rhFib in the milk of three transgenic heifers (#462, #463, #474) upon treatment of warfarin. Concentrations are in mg/ml raw milk as determined by ELISA. On day 1, warfarin treatment was started. Clot scores and amount of milk that was produced by each animal were monitored on a daily basis.

| Heifer | Day | Clot score | Amount of milk (lbs) | rhFib level |
|---|---|---|---|---|
| 462 | 1 | 3 | 12 | 1.3 |
| | 2 | 2.5 | 13 | |
| | 3 | 2.5 | 12 | |
| | 4 | 2.25 | 9.5 | |
| | 5 | 2 | 13 | |
| | 6 | 1 | 13 | |
| | 7 | 1 | 14 | |
| | 8 | 1 | 14 | |
| | 9 | 1 | 13.5 | |
| | 10 | 1 | 13 | 2.09 |
| | 37 | 0 | 14 | |
| 463 | 1 | 1.5 | 4 | 1.61 |
| | 2 | 2 | 4 | |
| | 3 | 2 | 4 | |
| | 4 | 3 | 4 | |
| | 5 | 2.5 | 4.5 | |
| | 6 | 2.5 | 5 | |
| | 7 | 1.25 | 5.5 | |
| | 8 | 1 | 6 | |
| | 9 | 1 | 6 | |
| | 10 | 1 | 6 | 2.47 |
| | 37 | 0 | 6.5 | |
| 474 | 1 | 3 | 9.5 | 0.41 |
| | 2 | 3 | 8 | |
| | 3 | 3 | 9 | |
| | 4 | 2 | 8 | 0.58 |
| | 5 | 1 | 8 | |
| | 6 | 1 | 7.5 | |
| | 7 | 1 | 7.5 | |
| | 37 | 0 | 8.5 | |

Example 4

Treatment of rhFib Transgenic Heifers with Warfarin During Natural Lactation

In example 2, seven transgenic rhFib cattle were induced to lactate by chemical means. However, that is not a natural situation. The rhFib protein is under normal circumstances produced in milk after natural lactation, which is: upon pregnancy. To see whether high clot scores in cattle after a normal pregnancy could also be prevented by the administration of anticoagulants, such as warfarin, four heifers (#480: 'Flitter', #474: 'Freya', #462: 'Fantasia' and #469: 'Floss') and one cow (#60: 'Foxette') fulfilled a normal pregnancy period after which normal lactation started. As can be seen in Table IV, which shows the highest clot scores detected in any or more of the four quarters of each animal, all these clot scores were found to be zero on day 1, after which scores started to increase in subsequent milking days. Warfarin treatment started immediately after delivery with a dose of 0.10 mg/kg. As can be seen in Table IV, the highest scores all dropped to a level of 0-1 after a few days. Where highest scores were found to be 1, this rate resulted in no complications in getting the milk out of the quarter during the milking process. All animals did not show any adverse reactions from the warfarin treatment and all milk was easily removed from each of their four quarters each day as long as scoring continued. With respect to #60, the warfarin dose was increased on day 110 up to a maximum of 0.15 mg/kg. For #480, warfarin dose was increased on day 84, for #474 it was increased on day 97 and for #469, the dose was increased on day 44, never increasing above 0.15 mg/kg. Heifer #462 was taken off warfarin from day 13 to 16 because the animal suffered from winter dysentery and on day 30 because the animal underwent an abdominal surgery. After the disease as well as the surgery, the heifer fully recovered.

Milking continues until the natural lactation stops, and at that stage also warfarin treatment is stopped.

It is concluded from this data that also during natural lactation, as compared to lactation induction, treatment with an anticoagulant such as warfarin results in lactations of rhFib cows in which their milk can be removed from their udders without any difficulties and that clot scores drop to levels that are 1 or even down to 0.

TABLE IV

Highest clot scores detected in the milk of one rhFib transgenic cow (#60: 'Foxette') and four rhFib-transgenic heifers (#480: Flitter, #474: 'Freya', #462: 'Fantasia' and #469: 'Floss') when warfarin was administered directly upon delivery after a normal pregnancy, measured from the day that the animals started to lactate (day 1).

| Days in milk | #60 Foxette | #480 Flitter | #474 Freya | #462 Fantasia | #469 Floss |
|---|---|---|---|---|---|
| 1 | 0 | 0 | 0 | 0 | 2 |
| 2 | 0 | 3 | 2 | 1 | 3 |
| 3 | 0 | 3 | 1 | 2 | 3 |
| 4 | 2 | 3 | 2 | 1 | 3 |
| 5 | 2 | 2 | 1 | 1 | 3 |
| 6 | 2 | 2 | 1 | 1 | 3 |
| 7 | 2 | 2 | 1 | 0 | 3 |
| 8 | 2 | 3 | 1 | 0 | 2 |
| 9 | 2 | 1 | 1 | 0 | 2 |
| 10 | 2 | 0 | 1 | 0 | 2 |
| 11 | 2 | 0 | 1 | 0 | 2 |
| 12 | 1 | 0 | 1 | 0 | 2 |
| 13 | 2 | 0 | 1 | 0 | 2 |
| 14 | 1 | 0 | 0 | 0 | 1 |
| 15 | 1 | 0 | 0 | 0 | 1 |
| 16 | 2 | 1 | 0 | 1 | 1 |
| 17 | 1 | 0 | 0 | 1 | 1 |
| 18 | 2 | 0 | 0 | 1 | 1 |
| 19 | 2 | 0 | 0 | 1 | 0 |
| 20 | 1 | 0 | 0 | 1 | 0 |
| 21 | 1 | 0 | 0 | 1 | 0 |
| 22 | 1 | 1 | 0 | 1 | 0 |
| 23 | 1 | 1 | 0 | 1 | 0 |
| 24 | 1 | 1 | 0 | 1 | 0 |

TABLE IV-continued

Highest clot scores detected in the milk of one rhFib transgenic cow (#60: 'Foxette') and four rhFib-transgenic heifers (#480: Flitter, #474: 'Freya', #462: 'Fantasia' and #469: 'Floss') when warfarin was administered directly upon delivery after a normal pregnancy, measured from the day that the animals started to lactate (day 1).

| Days in milk | #60 Foxette | #480 Flitter | #474 Freya | #462 Fantasia | #469 Floss |
|---|---|---|---|---|---|
| 25 | 1 | 1 | 0 | 1 | 0 |
| 26 | 1 | 0 | 0 | 1 | 0 |
| 27 | 1 | 0 | 0 | 1 | 0 |
| 28 | 1 | 0 | 0 | 0 | 0 |
| 29 | 1 | 0 | 0 | 0 | 1 |
| 30 | 1 | 0 | 0 | 0 | 0 |
| 31 | 1 | 0 | 0 | 0 | 0 |
| 32 | 1 | 0 | 0 | 0 | 0 |
| 33 | 1 | 0 | 0 | 0 | 0 |
| 34 | 0 | 0 | 0 | 0 | 0 |
| 35 | 0 | 0 | 0 | 0 | 0 |
| 36 | 0 | 0 | 0 | 0 | 0 |
| 37 | 1 | 0 | 0 | 0 | 0 |
| 38 | 1 | 0 | 0 | 0 | 0 |
| 39 | 1 | 0 | 0 | 0 | 0 |
| 40 | 1 | 0 | 0 | 0 | 0 |
| 41 | 1 | 0 | 0 | 0 | 0 |
| 42 | 1 | 0 | 0 | 0 | 0 |
| 43 | 1 | 0 | 0 | 0 | 1 |
| 44 | 1 | 0 | 0 | 0 | 1 |
| 45 | 1 | 0 | 0 | 0 | 0 |
| 46 | 1 | 0 | 0 | 0 | 1 |
| 47 | 1 | 0 | 0 | 0 | 0 |
| 48 | 1 | 0 | 0 | 0 | 0 |
| 49 | 1 | 0 | 0 | 0 | 0 |
| 50 | 1 | 0 | 0 | 0 | |
| 51 | 1 | 0 | 0 | 0 | |
| 52 | 1 | 0 | 0 | 0 | |
| 53 | 1 | 0 | 0 | 0 | |
| 54 | 1 | 0 | 0 | 0 | |
| 55 | 1 | 0 | 0 | 0 | |
| 56 | 1 | 0 | 0 | 0 | |
| 57 | 1 | 0 | 0 | 0 | |
| 58 | 0 | 0 | 0 | 0 | |
| 59 | 0 | 0 | 0 | 0 | |
| 60 | 0 | 0 | 0 | 0 | |
| 61 | 0 | 0 | 0 | 1 | |
| 62 | 1 | 0 | 0 | 1 | |
| 63 | 0 | 0 | 0 | 0 | |
| 64 | 0 | 0 | 0 | 0 | |
| 65 | 0 | 0 | 0 | 0 | |
| 66 | 0 | 0 | 0 | 0 | |
| 67 | 0 | 0 | 0 | 0 | |
| 68 | 0 | 0 | 0 | 0 | |
| 69 | 0 | 0 | 0 | 0 | |
| 70 | 0 | 0 | 0 | 0 | |
| 71 | 0 | 0 | 0 | 0 | |
| 72 | 0 | 0 | 0 | 0 | |
| 73 | 0 | 0 | 0 | 0 | |
| 74 | 0 | 0 | 0 | 0 | |
| 75 | 0 | 0 | 0 | 0 | |
| 76 | 0 | 0 | 0 | 0 | |
| 77 | 0 | 1 | 0 | 1 | |
| 78 | 0 | 1 | 0 | 0 | |
| 79 | 0 | 1 | 0 | 0 | |
| 80 | 0 | 1 | 0 | 0 | |
| 81 | 0 | 2 | 0 | 0 | |
| 82 | 0 | 1 | 0 | 0 | |
| 83 | 0 | 1 | 0 | | |
| 84 | 0 | 1 | 0 | | |
| 85 | 0 | 1 | 0 | | |
| 86 | 0 | 1 | 0 | | |
| 87 | 0 | 1 | 0 | | |
| 88 | 0 | 1 | 0 | | |
| 89 | 0 | 0 | 0 | | |
| 90 | 0 | 0 | 0 | | |
| 91 | 0 | 1 | 0 | | |
| 92 | 0 | 1 | 0 | | |
| 93 | 0 | 0 | 0 | | |
| 94 | 0 | 0 | 0 | | |
| 95 | 0 | 0 | 0 | | |
| 96 | 0 | 0 | 0 | | |
| 97 | 0 | 0 | 0 | | |
| 98 | 0 | 0 | 1 | | |
| 99 | 0 | 0 | 0 | | |
| 100 | 0 | 0 | 0 | | |
| 101 | 0 | 0 | 1 | | |
| 102 | 0 | 0 | 1 | | |
| 103 | 0 | 0 | 1 | | |
| 104 | 0 | 0 | 1 | | |
| 105 | 0 | 0 | | | |
| 106 | 0 | 0 | | | |
| 107 | 0 | 0 | | | |
| 108 | 0 | 0 | | | |
| 109 | 0 | 0 | | | |
| 110 | 1 | 0 | | | |
| 111 | 1 | | | | |
| 112 | 0 | | | | |
| 113 | 0 | | | | |
| 114 | 0 | | | | |
| 115 | 0 | | | | |
| 116 | 0 | | | | |

REFERENCES

Prowse C V, Mattock P, Esnouf M P and A M Russell A M (1976) A variant of Prothrombin induced in cattle by prolonged administration of Warfarin. Biocheimica et Biophysica Act 434, 265-279

Smith K L and Schanbacher F L (1973) Hormone Induced Lactation in the Bovine. I. Lactational Performance Following Injections of 17β-Estradiol and Progesterone1. J of Dairy Science 56 (6), 738-743

The invention claimed is:

1. A method for the production of a recombinant blood clotting factor in the milk of a transgenic animal, wherein said recombinant blood dotting factor is recombinant human Fibrinogen (rhFib), wherein said animal is transgenic for said recombinant blood clotting factor and wherein said recombinant blood clotting factor is expressed in the milk of said transgenic animal, comprising the steps of:
   starting lactation in said animal;
   administering an anticoagulant to said animal, wherein said anticoagulant is a coumarin-derived anticoagulant;
   harvesting from said animal the milk containing said recombinant blood clotting factor.

2. The method according to claim 1, wherein said animal is a cow, a sheep, a goat, a rabbit, a pig or a mouse.

3. The method according to claim 2, wherein said animal is a cow.

4. The method according to claim 1, wherein said starting of lactation is naturally by calving, or synthetically induced by administering chemicals and/or hormones.

5. The method according to claim 1, wherein said anticoagulant is warfarin, acenocoumarol, or phenprocoumon.

6. The method according to the claim 1, wherein said coumarin-derived anticoagulant is warfarin.

7. The method according to claim 6, wherein the warfarin is administered in a dose between about 0.010 mg/kg/day and about 0.18 mg/kg/day.

8. The method according to claim 1, wherein said anticoagulant is administered orally to said animal.

9. The method according to claim 1, wherein a mixture of coumarin-derived anticoagulants is administered to said animal.

10. The method according to claim 1, further comprising the step of determining the degree of clots and flakes in the milk of said animal.

11. A method for the treatment of an animal that is transgenic for a recombinant blood clotting factor, wherein said recombinant blood clotting factor is recombinant human Fibrinogen (rhFib), wherein said treatment inhibits precipitation of said recombinant blood clotting factor, wherein said recombinant blood clotting factor is produced in the milk of said animal, comprising the steps of:
   starting lactation in said animal; and
   administering an anticoagulant to said animal, wherein said anticoagulant is a coumarin-derived anticoagulant.

12. The method according to claim 11, further comprising the step of determining the degree of clots and flakes in the milk of said animal.

13. The method according to claim 7, wherein the warfarin is administered in a dose between about 0.10 mg/kg/day and about 0.14 mg/kg/day.

14. The method according to claim 7, wherein the warfarin is administered in a dose between about 0.10 mg/kg/day and about 0.13 mg/kg/day.

15. The method according to claim 1, further comprising purifying said recombinant blood clotting factor from the harvested milk.

* * * * *